United States Patent
DeFrancesco et al.

(10) Patent No.: US 9,931,253 B2
(45) Date of Patent: Apr. 3, 2018

(54) CONTOURED ABSORBENT PAD

(71) Applicants: Stephen DeFrancesco, Pittsburgh, PA (US); Megan DeFrancesco, Pittsburgh, PA (US)

(72) Inventors: Stephen DeFrancesco, Pittsburgh, PA (US); Megan DeFrancesco, Pittsburgh, PA (US)

( * ) Notice: Subject to any disclaimer, the term of this patent is extended or adjusted under 35 U.S.C. 154(b) by 777 days.

(21) Appl. No.: 14/141,271

(22) Filed: Dec. 26, 2013

(65) Prior Publication Data

US 2014/0188065 A1 Jul. 3, 2014

Related U.S. Application Data

(60) Provisional application No. 61/746,715, filed on Dec. 28, 2012.

(51) Int. Cl.
| | |
|---|---|
| *A61F 13/15* | (2006.01) |
| *A61F 13/494* | (2006.01) |
| *A61F 13/475* | (2006.01) |
| *A61F 13/505* | (2006.01) |
| *A61F 13/539* | (2006.01) |
| *A61F 13/53* | (2006.01) |
| *A61F 13/45* | (2006.01) |
| *A61F 13/49* | (2006.01) |
| *A61F 13/472* | (2006.01) |

(52) U.S. Cl.
CPC .... *A61F 13/49466* (2013.01); *A61F 13/4758* (2013.01); *A61F 13/505* (2013.01); *A61F 13/45* (2013.01); *A61F 13/47236* (2013.01); *A61F 13/47272* (2013.01); *A61F 13/49058* (2013.01); *A61F 13/539* (2013.01); *A61F 2013/49486* (2013.01); *A61F 2013/530437* (2013.01)

(58) Field of Classification Search
CPC .. A61F 13/539; A61F 13/45; A61F 13/47236; A61F 13/47272; A61F 13/49058; A61F 2013/530437
USPC .............. 604/385.17, 385.101, 385.14
See application file for complete search history.

(56) References Cited

U.S. PATENT DOCUMENTS

| | | | |
|---|---|---|---|
| 2004/0092902 A1* | 5/2004 | Hoffman | A61F 13/495 604/385.101 |
| 2005/0148972 A1* | 7/2005 | Miyama | A61F 13/4704 604/380 |
| 2010/0057034 A1* | 3/2010 | Dennis | A61F 13/15203 604/385.05 |
| 2011/0004179 A1* | 1/2011 | Kurihara | A61F 13/4704 604/385.02 |

* cited by examiner

*Primary Examiner* — Jacqueline Stephens
(74) *Attorney, Agent, or Firm* — Cohen & Grigsby, P.C.

(57) ABSTRACT

A contoured absorbent pad for a diaper comprising a liquid permeable inner layer, impermeable outer layer, and a moulded absorbent core. The inner and outer layers are adhered together with the moulded absorbent core located between the inner and outer layers. The absorbent core includes fibers and superabsorbent materials and is moulded in a shape that is contoured to complement the human anatomy in the area of the upper buttocks and lower back.

20 Claims, 7 Drawing Sheets

CONTOURED ABSORBENT PAD

BACKGROUND OF THE INVENTION

Field of the Invention

The present invention relates generally to the field of diapers, and more specifically, to absorbent pads that augment the structure of diapers.

Description of the Related Art

Various articles configured for the absorption of body fluids such as urine and feces are well known. Examples include diapers, sanitary napkins, incontinent pads, and the like. These absorbent articles are disclosed in the literature and are available in the marketplace.

Absorbent articles typically comprise a liquid permeable inner layer, a liquid impermeable outer layer, and an absorbent layer that is located between the layers. The inner layer allows liquid to pass through to the absorbent layer where it is then accumulated. The outer layer serves as a moisture barrier preventing leakage to a garment. Use of adhesive to attach an absorbent article, such as a feminine pad, to a garment is also well known.

Absorbent articles such as diapers comprise an absorbent layer configured to fit in the crotch area between an infant's or individual's legs. A common problem with this design has been its inability to absorb and retain unusually large quantities of liquid that flow beyond the absorbent layer, primarily towards the upper-rear portion of the diaper.

In addition to the lack of absorbency in the upper-rear portion, diapers and absorbent pads do not closely follow the anatomical contours of the lower back, thus leaving an opening along the spine where liquids may escape.

Some prior articles such as incontinent pads, sanitary napkins, feminine pads, and the like tailor to liquid absorption in the crotch area. However, those articles have been found to be anatomically unsuited for use elsewhere on the human body, thus impairing absorbency results. Deforming such articles to apply them elsewhere on the human body affords some absorption capability, but they still lack an appropriately contoured fit and typically result in leakage.

Prior art designs do not adequately manage the problem of fluid leakage, particularly around the upper buttocks and lower back area. There is, therefore, a need for an absorbent article that contours to this area of the body and reliably prevents leakage.

SUMMARY OF THE INVENTION

The presently disclosed invention is directed to a contoured absorbent pad. It includes a liquid permeable inner sheet, a liquid impermeable outer sheet, and a moulded absorbent core that is located between the inner and outer sheets. The moulded absorbent core is contoured in thickness to have an elevated area that defines two sides and a base edge. The two sides are joined at one end and diverge from each other at their opposite ends. The base edge is located between the divergent ends of the two sides. The liquid impermeable sheet further includes an adhesive band for securing the absorbent pad to a diaper.

Preferably, the inner and outer sheets of the contoured absorbent pad define respective perimeters of substantially the same size and shape. The inner and outer sheets are bound together along a band that forms a closed pattern adjacent to the perimeters of the inner and outer sheets. The moulded absorbent core defines a perimeter that extends adjacent to the inside edge of the band formed by the juncture of the inner and outer sheets.

More preferably, the base edge of the moulded absorbent core defines an edge of the elevated area that includes a peak. The peak of the base edge is located to include the midpoint location between the divergent ends of the two sides of the elevated area of the moulded absorbent core. The peak extends from the midpoint location outwardly in a direction away from the two sides of the elevated area.

DETAILED DESCRIPTION OF THE INVENTION

Figure 1:
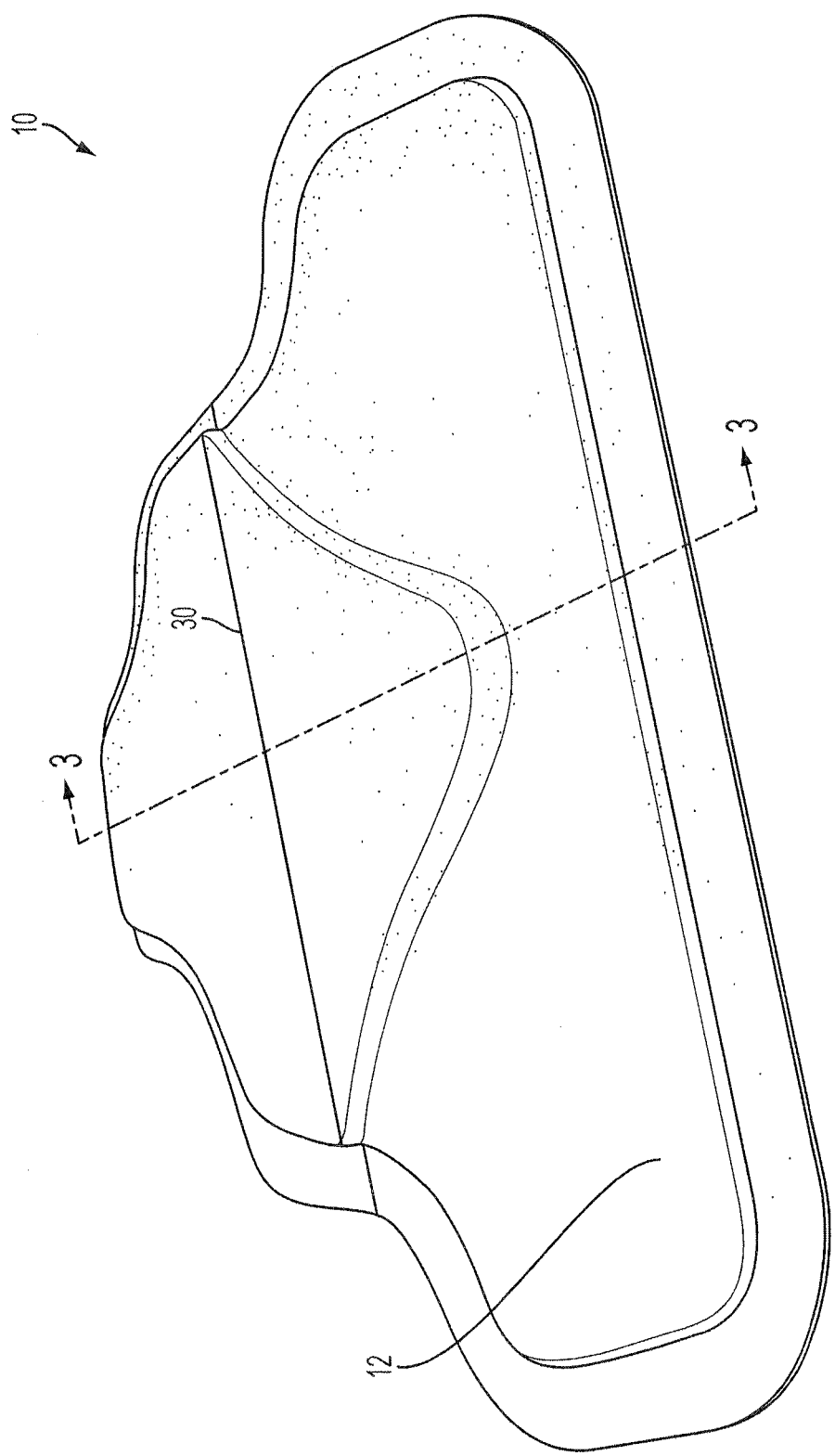
FIG. 1 is a perspective view of the contoured absorbent pad herein disclosed.

FIG. 1 is a perspective view of an embodiment of the presently disclosed contoured absorbent pad 10. The pad 10 includes an inner sheet 12 that is bonded to an outer sheet (shown in FIGS. 1 and 3). A moulded absorbent core 32 (shown in FIGS. 2, 3 and 5) is located between the inner and outer sheets.

Figure 2:
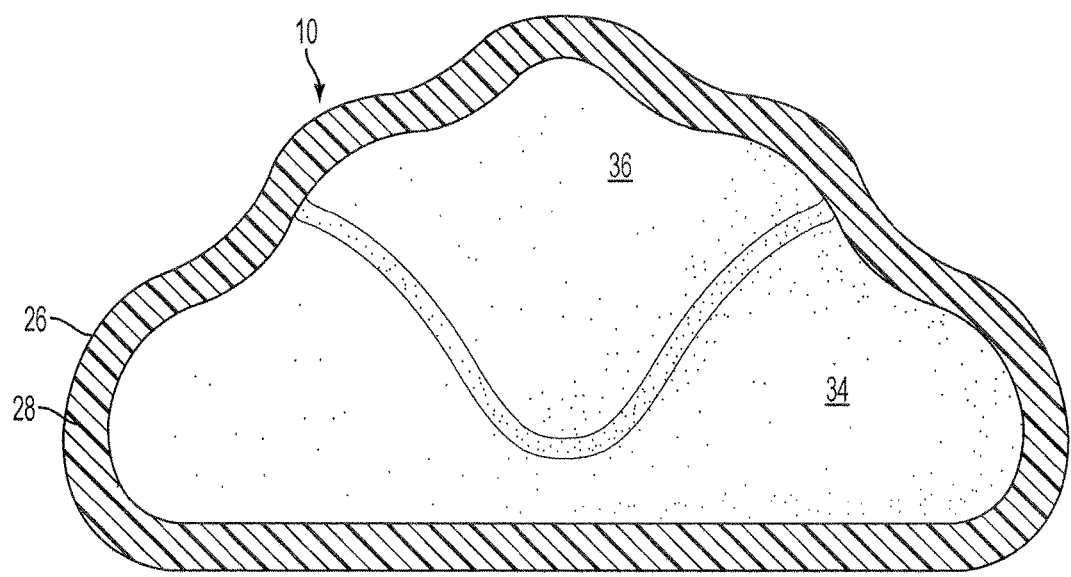
FIG. 2 is a top plan view of the embodiment of the presently disclosed invention shown in FIG. 1 with the inner sheet removed.
Figure 3:
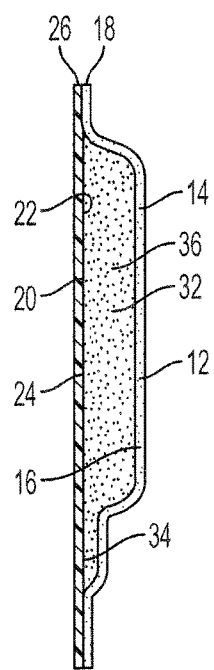
FIG. 3 is a cross-section of the embodiment of FIG. 1 taken along the lines 3-3 of FIG. 1.

FIG. 2 shows an embodiment of the contoured absorbent pad 10 from the side of the inner sheet 12, but with the inner sheet removed. FIG. 3 is a cross-sectional view of the pad shown in FIG. 1 taken along the line 3-3 of FIG. 1. The contours of the inner sheet 12 are due to the features of moulded absorbent core 32 and are shown by shading of the inner sheet surface 14. As shown in FIGS. 1 and 3, inner sheet 12 has first and second oppositely disposed major surfaces 14, 16 and a peripheral edge 18 between the first and second major surfaces. The inner sheet 12 is comprised of a liquid permeable material such a Whitening perforated non-woven.

Figure 4:
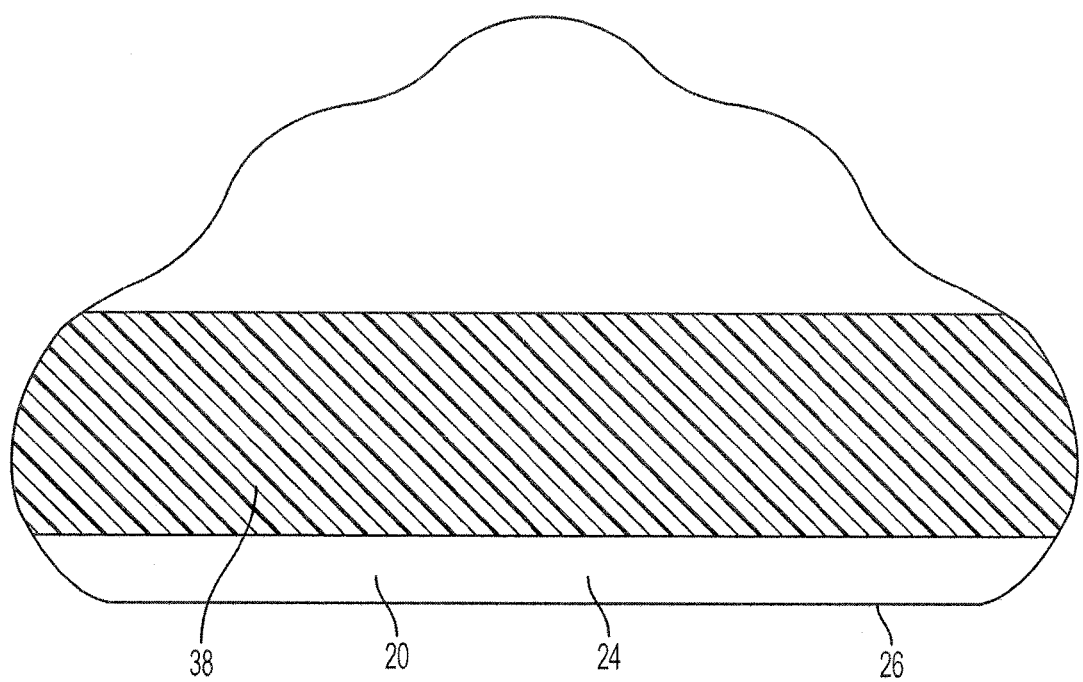
FIG. 4 is a bottom plan view of the embodiment of FIGS. 1-3.

FIG. 4 shows the contoured absorbent pad 10 of FIGS. 1-3 taken from the side of the outer sheet 20. FIGS. 3 and 4 show that outer sheet 20 has first and second oppositely disposed major surfaces 22, 24 that define a peripheral edge 26 of the outer sheet 20 between the first and second major surfaces 22, 24. Outer sheet 20 is made of a liquid impermeable material such as PE film.

Second surface 16 of the inner sheet 12 that is adjacent to the peripheral edge 18 of the inner sheet 12 contacts the first surface 22 of the outer sheet 20 at a location that is adjacent the peripheral edge 26 of the outer sheet 20. The area of the outer sheet 20 that contacts the inner sheet 12 defines a band 28 that is a closed boundary inside the peripheral edges 26, 18 of outer sheet 20 and inner sheet 12. In certain embodiments, band 28 is a seam between the inner, liquid permeable sheet 12 and the outer, liquid impermeable sheet 20 that is made by hot pressing the portions of inner sheet 12 within band 28 together with portions of outer sheet 20 that also are within band 28.

As particularly shown in FIGS. 2 and 3, a moulded absorbent core 32 of high absorbent material is enveloped between the second surface 16 of inner sheet 12 and the first surface 22 of outer sheet 20. The super absorbent material of the moulded absorbent core 32 is located inside closed band 28 that is formed between inner and outer sheets 12, 20. Moulded absorbent core 32 is comprised of high absorbent material such as American fluff pulp, San-Dia SAP, and airliad paper, either alone or in combination. Moulded absorbent core 32 is located within the closed boundary of band 28 and complements the peripheral edges 18, 26 of inner and outer sheets 12, 20.

Figure 5:
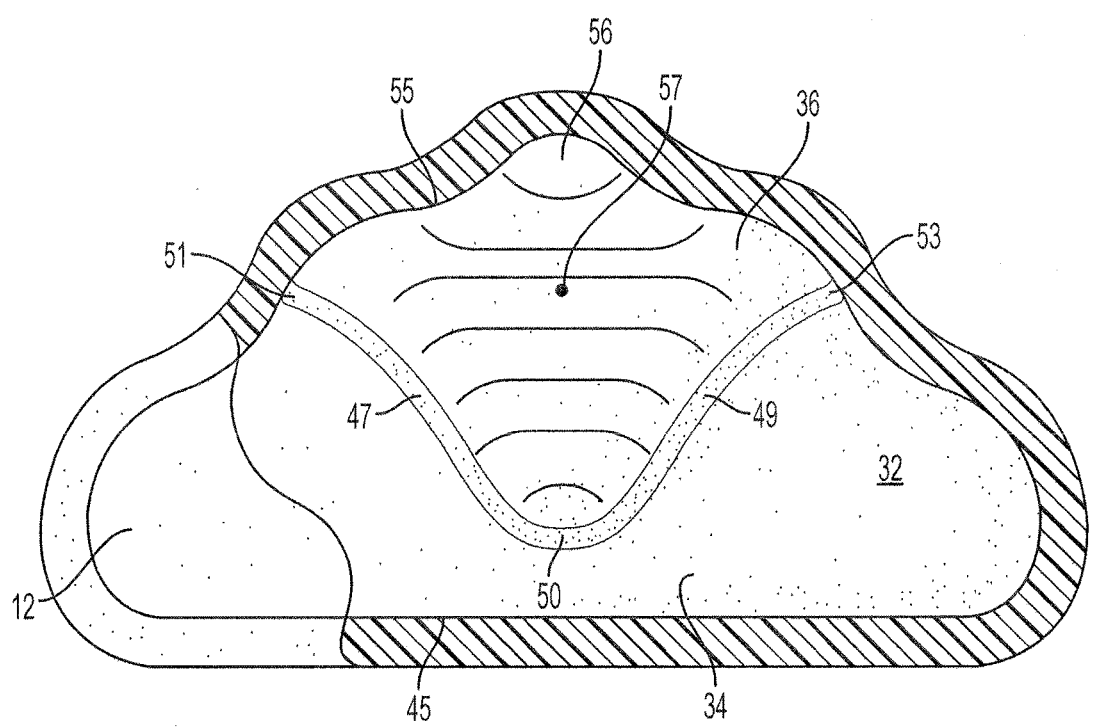
FIG. 5 is a view of the contoured absorbent pad as shown in FIG. 1 with portions of the inner sheet thereof broken away to better show internal structure.

FIG. 5 shows the embodiment of the contoured absorbent pad 10 of FIGS. 1-4 with a portion of inner sheet 12 broken away to better disclose the moulded absorbent core 32. As shown more particularly in FIG. 5, moulded absorbent core 32 defines a relief area 34 that partially surrounds an elevated area 36. FIG. 5 is shaded to show the contours of the absorbent core 32 including the raised or elevated area 36 in the upper-middle portion of the moulded absorbent core 32. When in use, the raised or elevated area 36 of absorbent core 32 enables moulded absorbent core 32 to follow the contour of the upper buttocks and lower back area of the human anatomy. This provides a form fit that helps retain bodily fluids such as urine or feces.

As particularly shown in FIG. 5, moulded absorbent core 32 defines an outer perimeter 45 that is generally triangular. The elevated area 36 of moulded absorbent core 32 defines a first side 47 and a second side 49. First and second sides 47, 49 are oriented with respect to each other at an angle. Moving in one direction along either of sides 47, 49, the sides converge together and moving in the opposite direction along either side, the sides diverge away from each other. Sides 47, 49 join together at a junction 50 and terminate in in respective divergent ends 51, 53. Alternatively stated, moulded absorbent core 32 is contoured in thickness to have an elevated area 36 that defines two sides 47, 49. The two sides 47, 49 are joined at one end 50 and diverge from each other at the opposite ends 51, 53.

Elevated area 36 has a base edge 55 that extends between the divergent ends 51, 53 of first and second sides 47, 49. The base edge 55 of the moulded absorbent core 32 defines an edge of the elevated area 36 that includes a peak 56. The peak 56 of base side 55 is located adjacent to and including the midpoint location 57 between the divergent ends 51, 53 of sides 47, 49. Peak 56 extends from the midpoint location 57 outwardly in a direction away from the two sides 47, 49 of elevated area 36.

The contoured absorbent pad 10 disclosed herein defines two areas of respectively different thicknesses—the raised or elevated area 36 and area 34 that stands in relief to the elevated area. In the assembled contoured absorbent pad, the thickness dimension of elevated area 36 and relief area 34 is measured in a direction normal to the surface 22 of outer sheet 20. Moulded absorbent core 32 is formed such that typical dimensions of the raised area 36 are a thickness of 8 mm. The thickness of relief area 34 that stands in relief to elevated portion 36 is typically about 2.5 mm. Generally, it has been found that the ratio of the thickness of the elevated portion to the thickness of the relief portion is greater than 2:1 and ratios of 3:1 or greater are preferred.

In the presently disclosed invention, the shape of moulded absorbent core 32 is a moulded shape as opposed to a body formed of sheets of material that are stacked together. One reason that the moulded body of moulded absorbent core 32 is preferred is that the moulded body retains its shape even after absorbing fluids. This feature allows the moulded absorbent core 32 and the portions of the absorbent pad 10 that are in contact with the moulded absorbent core 32 to maintain their shape both before and after absorbing fluids so as to complement that area of the human anatomy in the region of the upper buttocks. The persistent shape of the moulded absorbent core 32 before and after absorbing fluids thus causes the contoured absorbent pad 10 to block the leakage of fluids between the contoured absorbent pad and the skin of the wearer both before and after the absorbent core 32 has absorbed fluid. Even after the absorbent core 32 has absorbed fluid to the point that it becomes saturated, it has been found that the moulded shape continues to block the passage of fluid so that it is retained in the diaper.

Also, embodiments of the presently disclosed invention include a contour of absorbent core 32 in which base edge 55 includes peak 56 that defines the part of the absorbent core that extends further from edges 47, 49 of elevated area 36. It has been found that the inclusion of peak 56 in base edge 55 further enhances the complementary fit of absorbent core to the human anatomy in the area above the buttocks and thereby further improves blockage of fluid flow between the pad 10 and the wearer.

The moulded shape of moulded absorbent core 32 is sufficiently elastic and pliable so that it can also conform to the movements of the wearer throughout a normal range of motion. Thus, the moulded shape of contoured pad 10 is comfortable for the wearer and also maintains contact with the wearer's skin through repeated extension and retraction movements of the wearer. In this way, contoured absorbent pad 10 blocks the flow of fluids between the contoured absorbent pad and the wearer's skin irrespective of the wearer's particular body position. It has been found that moulded absorbent core 32 in contoured pad 10 effectively blocks the passage of fluids between the contoured absorbent pad 10 and the wearer even when the wearer has assumed extreme or unusual body contortions in the time that the contoured absorbent pad is worn.

In a preferred embodiment, the contoured absorbent pad 10 is formed by cracking wood pulp into ashes. The ashes are then injected into a mould with an inner cavity that is shaped according to the features of the contoured absorbent pad 10. In some embodiments, it is preferred to further compress the moulded shape by a forming wheel or other device to impose secondary features such as relief area 34 in the moulded piece.

Figure 6:
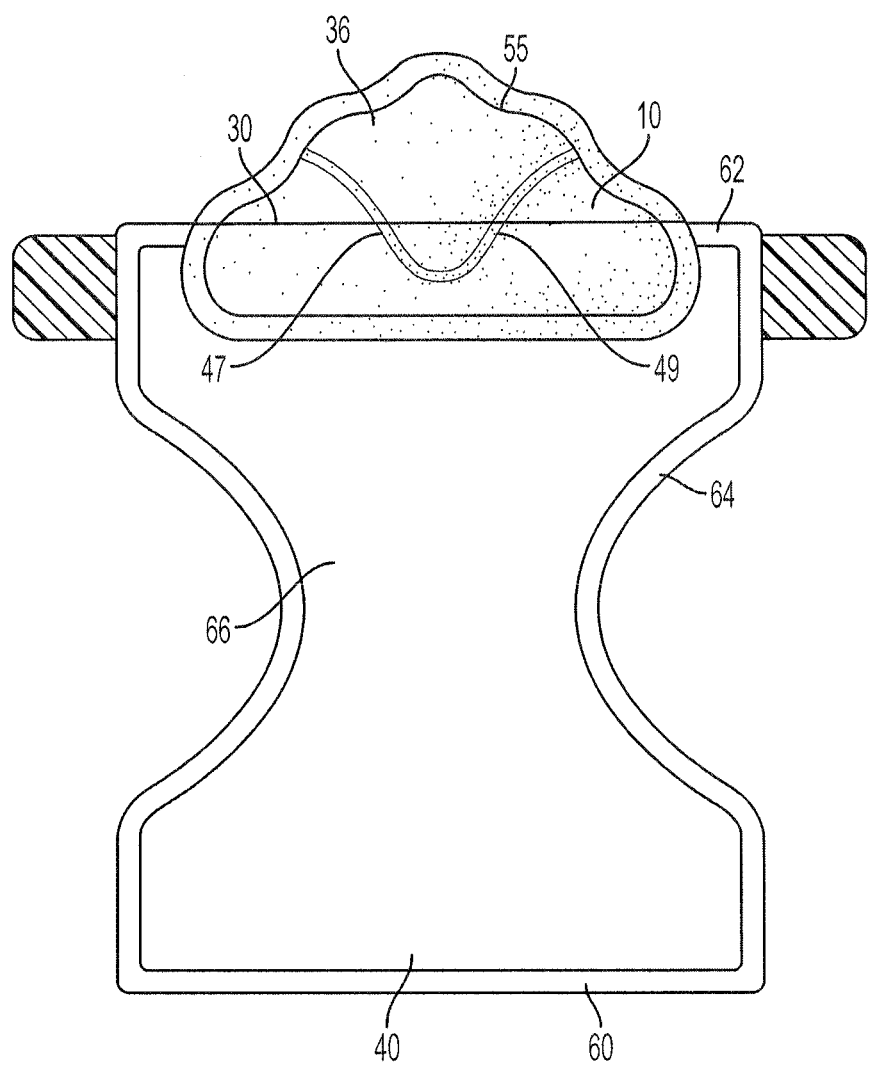
FIG. 6 is a plan view of the contoured absorbent pad shown in FIGS. 1-5 as applied to a diaper.

In some cases, core 10 is secured to the second surface 16 of inner sheet 12 with an adhesive. Also, in some embodiments, core 10 can be secured to the first surface 22 of outer sheet 20 with an adhesive, As illustrated in FIG. 6, the absorbent pad 10 is adhered to a diaper 40 with adhesive band 38. To assure proper alignment and location of the contoured absorbent pad 10 within a diaper, at least one of the inner and outer sheets 12, 20 includes an indicator 30 for aligning the contoured absorbent pad 10 with the back edge of the diaper.

Diaper 40 includes a liquid impermeable outer layer 64 and a liquid permeable inner layer 66. The contoured absorbent pad 10 is oriented with respect to diaper 40 such that adhesive layer or band 38 is connectable to the liquid permeable inner layer 66 of the diaper. The absorbent pad is adhered to the diaper with an adhesive band 38 that is located on surface 24 of outer sheet 20 as shown in FIG. 4. Adhesive band 38 extends the entire width of the pad 10. Prior to the application of pad 10 to diaper 40, adhesive band 38 is covered with a removable film. To install the absorbent pad inside the diaper, the removable film is peeled away to expose the adhesive band 38 and the pad is applied to diaper 40. Referring to FIG. 1, the solid line running the width of pad 10 is an alignment indicator 30. The alignment indicator 30 is to be aligned with the top-rear edge of the diaper.

In embodiments, diaper 40 defines a front edge 60 and a back edge 62 that is located on the diaper oppositely from the front edge. The contoured absorbent pad 10 is secured to diaper 40 such that at least a portion of the base side 55 of the moulded absorbent core 32 extends from diaper 40 outwardly past the back edge 62 of the diaper while at least a portion of the sides 47, 49 are within diaper 40 inside of back edge 62.

As shown in FIG. 6, indicator 30 is located such that at least a portion of base side 55 of elevated area 36 extends from diaper 40 outwardly beyond back edge 62 of the diaper. Also, indicator 30 is located such that at least a portion of the edges 47, 49 of elevated area 36 are located on diaper 40 inwardly from back edge 62.

Upon contact with inner layer 66, the exposed adhesive 38 holds the contoured absorbent pad 10 in place until the diaper is secured around the infant or adult. Once the diaper is secured around the infant or adult the adhesive will secure the pad 10 to the diaper 40, forming a tight seal between the pad and diaper. The contour of the pad forms a tight seal between the pad and the infant or adult.

Figure 7:
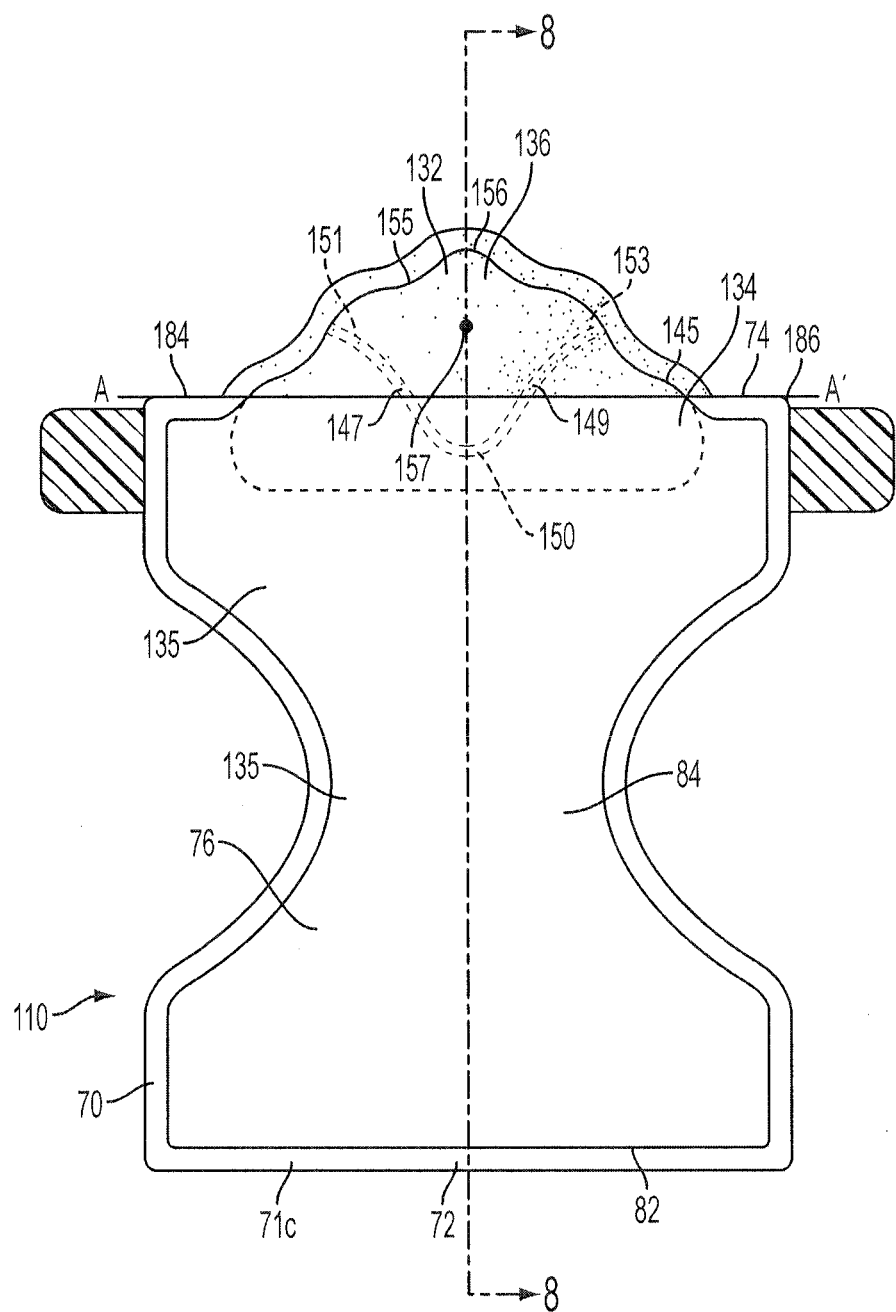
FIG. 7 is a plan view of an alternative embodiment of the presently disclosed invention wherein the contoured absorbent pad is integral with a diaper.
Figure 8:
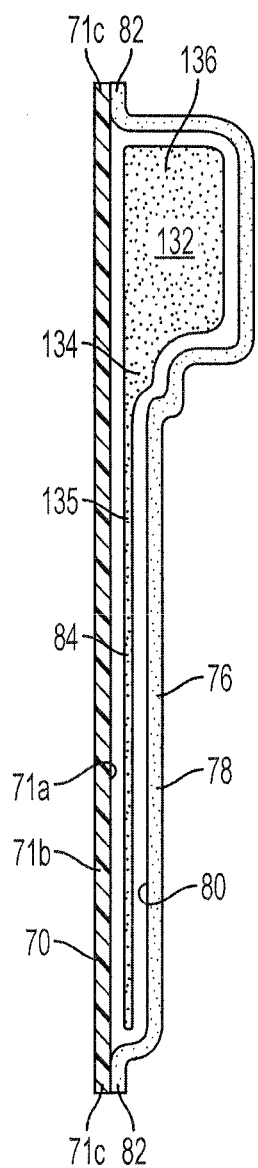
FIG. 8 is a cross-section of the alternative embodiment that is shown in FIG. 7.

The presently disclosed invention includes embodiments such as shown in FIGS. 7 and 8 wherein the moulded absorbent core is integrated with the absorbent layer of diaper 40. In some embodiments, the combination of the diaper and moulded absorbent core includes an outer sheet of liquid impermeable material 70. Outer sheet 70 has first and second oppositely disposed major surfaces 71a, 71b and defines a peripheral edge 71c. Peripheral edge 71c also serves as a perimeter for the diaper and defines a front edge 72 and a back edge 74 that is oppositely located from the front edge.

An inner sheet 76 that has first and second oppositely disposed major surfaces 78, 80 and defines a peripheral edge 82 for the inner sheet 76 between the first and second major surfaces 78, 80. Second surface 80 of the inner sheet 76 contacts the first surface 71a of the outer sheet 70 adjacent to their respective peripheral edges 71c and 82 such that the area of the outer sheet that contacts the inner sheet defines a closed boundary inside of the peripheral edge 82 of the inner sheet.

An inner absorbent layer or liner 84 is enveloped between outer sheet 70 and inner sheet 76. Liner 84 includes a moulded absorbent core 132 that defines an outer perimeter 145 that is generally triangular. Moulded absorbent core 132 includes an elevation area 136 and a recessed area 134. The elevated area 136 of moulded absorbent core 132 defines a first side 147 and a second side 149. First and second sides 147, 149 are oriented with respect to each other at an angle. Moving in one direction along either of sides 147, 149, the sides converge together and moving in the opposite direction along either side, the sides diverge away from each other. Sides 147, 149 join together at a junction 150 and terminate in in respective divergent ends 151, 153. Alternatively stated, moulded absorbent core 132 is contoured in thickness to have an elevated area 136 that defines two sides 147, 149. The two sides 147, 149 are joined at one end 150 and diverge from each other at the opposite ends 151, 153.

Elevated area 136 has a base edge 155 that extends between the divergent ends 151, 153 of first and second sides 147, 149. The base edge 155 of the moulded absorbent core 132 defines an edge of the elevated area 136 that includes a peak 156. The peak 156 of base side 155 is located adjacent the midpoint location 157 between the divergent ends 151, 153 of sides 147, 149. Peak 156 extends from the midpoint location 157 outwardly in a direction away from the two sides 147, 149 of elevated area 136.

The integrated contoured absorbent pad 110 in which the moulded absorbent core is integrated with the absorbent layer of diaper 40 as disclosed herein defines three areas of respectively different thicknesses—the raised or elevated area 136, an area 134 that stands in relief to the elevated area, and the remainder area 135 of liner 84. In the integrated contoured absorbent pad 110, the thickness dimension of elevated area 136, relief area 134, and remainder area 135 is measured in a direction normal to the surface 71b of outer sheet 70. Moulded absorbent core 132 is formed such that typical dimensions of the elevated area 136 are a thickness of 8 mm. The thickness of relief area 134 that stands in relief to elevated area 136 is typically about 2.5 mm. The thickness of the remainder area 143 of liner 84 is typically less than 2.5 mm. Generally, it has been found that the ratio of the thickness of the elevated portion 136 to the thickness of the relief portion 134 is greater than 2:1 and ratios of 3:1 or greater are preferred.

In still another embodiment, the thickness of the relief portion 134 can be decreased so that, in some cases, the thickness of the relief portion 134 is substantially the same as the thickness of the remainder area 135 of liner 84. In another embodiment, the thickness of the remainder area 135 can be increased so that, in some cases, the thickness of the remainder portion 135 is substantially the same as the thickness of the relief portion 134 shown in FIG. 8. In these alternative embodiments, the result is that the liner 84 effectively has only two different thicknesses—the thickness of the elevated area 136 and the thickness of the reset of the liner 84. In that case, the area that partially surrounds elevated area 136 can be moulded or it can be a continuation of the rest of the liner 84. Where the relief portion 134 is thicker than the remainder portion 135, it is preferred that the relief portion is moulded as is more specifically explained in connection with the embodiments of FIGS. 1-6. In all cases, it is preferred that the elevated area 136 is moulded as is more specifically explained in connection with the embodiments of FIGS. 1-6.

As shown in FIGS. 7 and 8, at least a portion of base side 155 of elevated area 136 extends from the back corners 184, 186 of diaper 140 in a direction outward from the diaper and beyond a straight line A-A' between corners 184, 186. Also, at least a portion of the edges 147, 149 of elevated area 136 are located on diaper 140 inwardly from the straight line A-A' between corners 184, 186.

Once the diaper is secured around the infant or adult, the contour of the integrated contoured absorbent pad 110 forms a tight seal between the pad and the infant or adult.

Although certain preferred embodiments of the present invention have been shown and described, it will be apparent to those skilled in the art that many changes and modifications may be made without departing from the invention in its broader aspects.

We claim:
1. A contoured absorbent pad in combination with a diaper, said diaper including a liquid impermeable outer layer and a liquid permeable inner layer, said diaper defining a front edge and a back edge that is located on said diaper oppositely from said front edge, said contoured absorbent pad comprising:

(a) an outer sheet having first and second oppositely disposed major surfaces that define a peripheral edge of said outer sheet between said first and second major surfaces, said outer sheet being made of a liquid impermeable material;
(b) an inner sheet that has first and second oppositely disposed major surfaces and that defines a peripheral edge of said inner sheet between said first and second major surfaces, the second surface of said inner sheet that is adjacent to the peripheral edge of said inner sheet contacting the first surface of said outer sheet at a location that is adjacent the peripheral edge of said outer sheet such that the area of said outer sheet that contacts said inner sheet defines a closed boundary along the peripheral edges of the outer sheet and the inner sheet;
(c) a moulded core of high absorbent material that is enveloped between the second surface of said inner sheet and the first surface of said outer sheet, said moulded core being located within the closed boundary along the peripheral edges of said outer and inner sheets, said moulded core including a first area that is a relief area and also including a second area that is an elevated area, said elevated area of said moulded core defining a first edge, a second edge, and a third edge that is a base edge, said relief area of said moulded core partially surrounding said elevated area of said moulded core and forming an edge between said moulded core and said elevated area wherein the thickness of said elevated area is more than two times the corresponding dimension of said relief area; and
(d) an adhesive layer that is located on the second surface of said outer sheet and said contoured absorbent pad is secured to said inner layer of the diaper such that the base side edge of said moulded core extends from said diaper outwardly past the back edge of said diaper.

2. The contoured absorbent pad of claim 1 wherein said first and second edges of said elevated area are angled with respect to each other such that said first and second edges converge together in a first direction and diverge away from each other in a direction that is opposite from said first direction to respectively form first and second divergent ends, the base edge of said elevated area extending between the first and second divergent ends of said first and second edges.

3. The contoured absorbent pad of claim 1 wherein said first and second edges of said elevated area are angled with respect to each other such that said first and second edges converge together at a junction in a first direction and diverge away from each other in a direction away from said junction to respectively form first and second divergent ends, the base edge of said elevated area extending between the first and second divergent ends of said first and second edges.

4. The contoured absorbent pad of claim 1 wherein said moulded core defines an outer perimeter that is in the general shape of a triangle.

5. The contoured absorbent pad of claim 1 wherein at least a portion of said first and second edges of said moulded core extend from said diaper inwardly from the back edge.

6. The contoured absorbent pad of claim 1 wherein at least one of said inner and outer sheets includes an indicator for orienting the contoured absorbent pad within said diaper.

7. The contoured absorbent pad of claim 1 wherein said inner sheet is made of liquid permeable material that is comprised of a perforated non-woven material.

8. The contoured absorbent pad of claim 1 wherein said liquid impermeable material of said outer sheet is comprised of polyethylene film.

9. The contoured absorbent pad of claim 7 wherein said liquid permeable inner sheet and said liquid impermeable outer sheet are joined at a seam formed by hot pressing portions of the inner sheet together with portions of the outer sheet.

10. The contoured absorbent pad of claim 1 wherein the moulded core is composed of one or more materials selected from the group comprising fluff pulp, sap and airlaid paper.

11. A diaper that incorporates a contoured absorbent pad comprising:
an outer sheet of liquid impermeable material, said outer sheet having first and second oppositely disposed major surfaces and defining a peripheral edge of said outer sheet between first and second major surfaces, said perimeter edge defining a front edge and a back edge that includes two back corners, said front edge being oppositely located on said outer sheet from said front edge between said two back corners;
an inner sheet that has first and second oppositely disposed major surfaces and that defines a peripheral edge of said inner sheet between said first and second major surfaces of said inner sheet, the second major surface of said inner sheet contacting the first major surface of said outer sheet such that the area of said outer sheet that contacts said inner sheet defines a closed boundary within the peripheral edge of said inner sheet; and
a layer of high absorbent material that is enveloped between the second surface of said inner sheet and the first surface of said outer sheet, said layer of high absorbent material being located within the closed boundary of said inner and outer sheets, said layer of high absorbent material including a moulded core of high absorption material that defines an elevated area wherein the thickness dimension of said elevated area is more than two times the thickness dimension of other portions of said layer of high absorbent material, the elevated area of said moulded high absorbent layer defining a first edge, a second edge, and a third edge, said first and second edges being oriented with respect to each other such that said first and second edges form a junction and diverge away from each other in a direction away from said junction to respectively form first and second divergent ends, the third edge of said elevated area of said moulded core defining a base edge that extends between the first and second divergent ends, said base edge extending away from the junction of said first and second edges such that the base edge of said moulded core extends outwardly past a straight line between said back corners of said outer sheet.

12. The diaper of claim 11 wherein said moulded core further includes a recessed area that partially surrounds said elevated area, said elevated area having a thickness that is at least twice the thickness of said recessed area.

13. The diaper of claim 12 wherein said recessed area has a thickness that is greater than the thickness of a portion of said layer of high absorbent material that is not included in said moulded core.

14. The diaper of claim 11 wherein the base edge of said elevated area of said moulded core further includes a peak area that extends further from the first and second edges than other portions of said base edge.

15. The diaper of claim 14 wherein said peak area is located to include the midpoint between said first and second divergent ends of said first edge and said second edge.

16. A contoured absorbent article incorporated into a diaper, where said absorbent article comprises:
a liquid-impermeable outer layer;
a liquid-permeable inner layer, and
a contoured, liquid absorbent, moulded core layer comprised of one or more materials, where the moulded core has a first area that is a relief area and also a second area that is an elevated area, said relief area partially surrounding said elevated area wherein the dimension of said elevated area measured in a direction perpendicular to a surface of said relief area is more than two times the corresponding dimension of said relief area, and wherein the elevated area of said moulded core defines a first edge, a second edge and a third edge, said first and second edges being angled with respect to each other such that said first and second edges converge together in a first direction and diverge away from each other in a direction that is opposite from said first direction to respectively form first and second divergent ends, the elevated area of said moulded core further defining a third edge that is a base edge that extends between the first and second divergent ends of said first and second edges leading to a perimeter that is in the general shape of a triangle, and wherein the said elevated area further includes a peak area that extends further from the first and second edges than other portions of the base edge.

17. The contoured absorbent article as set forth in claim 16 wherein the relief and elevated areas are intended to face and fit the area on a person's body located towards the top of the buttocks and below the lower back.

18. The contoured absorbent article of claim 16 wherein said diaper defines a front edge and a back edge that is located on said diaper oppositely from said front edge, said contoured absorbent article being secured to or incorporated within said diaper such that the base side of said moulded core extends from said diaper outwardly past or to, respectively, the back edge of said diaper.

19. The contoured absorbent article of claim 18 wherein at least a portion of said first and second edges of said moulded core extend from said diaper inwardly from the back edge of said diaper.

20. The contoured absorbent article of claim 19 wherein at least one of said inner and outer layers includes an indicator for orienting the contoured absorbent article within said diaper.

* * * * *